United States Patent [19]
Nieendick et al.

[11] Patent Number: 5,712,235
[45] Date of Patent: Jan. 27, 1998

[54] BAR SOAPS

[75] Inventors: Claus Nieendick, Krefeld; Gerhard Wollmann, Hilden; Bernd Richter, Leichlingen; Karl-Heinz Schmid, Mettmann; Andreas Syldath, Duesseldorf; Bernd Fabry, Korschenbroich, all of Germany

[73] Assignee: Henkel Kommanditgesellschaft auf Aktien, Duesseldorf, Germany

[21] Appl. No.: 617,906

[22] PCT Filed: Sep. 6, 1994

[86] PCT No.: PCT/EP94/02968

§ 371 Date: Mar. 15, 1996

§ 102(e) Date: Mar. 15, 1996

[87] PCT Pub. No.: WO95/07975

PCT Pub. Date: Mar. 23, 1995

[30] Foreign Application Priority Data

Sep. 15, 1993 [DE] Germany ............... 43 31 297.7

[51] Int. Cl.$^6$ ............... C11D 1/68; C11D 1/74; C11D 3/22

[52] U.S. Cl. ............... 510/151; 510/152; 510/155; 510/156

[58] Field of Search ............... 510/130, 141, 510/152, 155, 156, 151

[56] References Cited

U.S. PATENT DOCUMENTS

| | | | |
|---|---|---|---|
| 1,985,424 | 3/1934 | Piggott | 260/124 |
| 2,016,962 | 10/1935 | Flint et al. | 260/127 |
| 2,703,798 | 3/1955 | Schwartz | 260/211 |
| 4,536,318 | 8/1985 | Cook et al. | 252/174.17 |
| 4,599,188 | 7/1986 | Llenado | 252/174.17 |
| 5,009,814 | 4/1991 | Kelkenberg et al. | 252/548 |
| 5,043,091 | 8/1991 | Joshi et al. | 252/174.17 |
| 5,227,086 | 7/1993 | Kacher et al. | 252/112 |
| 5,254,281 | 10/1993 | Pichardo et al. | 252/108 |
| 5,262,079 | 11/1993 | Kacher et al. | 252/112 |
| 5,312,932 | 5/1994 | Behler et al. | 554/90 |
| 5,319,117 | 6/1994 | Fabry et al. | 554/98 |
| 5,322,957 | 6/1994 | Fabry et al. | 558/23 |
| 5,374,716 | 12/1994 | Biermann et al. | 536/18.6 |

FOREIGN PATENT DOCUMENTS

| | | |
|---|---|---|
| 0070075 | 1/1983 | European Pat. Off. . |
| 0176330 | 4/1986 | European Pat. Off. . |
| 0189332 | 7/1986 | European Pat. Off. . |
| 0227321 | 7/1987 | European Pat. Off. . |
| 0285768 | 10/1988 | European Pat. Off. . |
| 0301298 | 2/1989 | European Pat. Off. . |
| 0308189 | 3/1989 | European Pat. Off. . |
| 308190 | 3/1989 | European Pat. Off. . |
| 0358216 | 3/1990 | European Pat. Off. . |
| 0459769 | 12/1991 | European Pat. Off. . |
| 0463912 | 1/1992 | European Pat. Off. . |
| 0472320 | 2/1992 | European Pat. Off. . |
| 0508006 | 10/1992 | European Pat. Off. . |
| 1580491 | 9/1969 | France . |
| 593422 | 2/1931 | Germany . |
| 4016819 | 12/1991 | Germany . |
| WO 903977 | 4/1990 | WIPO . |
| WO9106532 | 5/1991 | WIPO . |
| WO9113896 | 9/1991 | WIPO . |
| WO9119009 | 12/1991 | WIPO . |
| WO 926155 | 4/1992 | WIPO . |
| WO 926161 | 4/1992 | WIPO . |
| WO 926162 | 4/1992 | WIPO . |
| WO 926164 | 4/1992 | WIPO . |
| WO 926170 | 4/1992 | WIPO . |
| WO 926171 | 4/1992 | WIPO . |
| WO 926172 | 4/1992 | WIPO . |
| WO 926154 | 4/1992 | WIPO . |
| WO 926160 | 4/1992 | WIPO . |
| WO 926159 | 4/1992 | WIPO . |
| WO 926158 | 4/1992 | WIPO . |
| WO 926152 | 4/1992 | WIPO . |
| WO9206984 | 4/1992 | WIPO . |
| WO 926157 | 4/1992 | WIPO . |
| WO 926156 | 4/1992 | WIPO . |
| WO 926153 | 4/1992 | WIPO . |
| WO9209570 | 6/1992 | WIPO . |
| WO9209569 | 6/1992 | WIPO . |
| WO9213059 | 8/1992 | WIPO . |
| WO9310084 | 5/1993 | WIPO . |

OTHER PUBLICATIONS

Chemical Abstract 119:162925h, vol. 119, 1993, p. 158 No month available.
J. Am. Oil. Chem. Soc. 59, 442 (1982).
Tens. Surf. Det. 25, 8 (1988).
J. Falbe (ed.), "Surfactants in Consumer Products", Springer Verlag, Berlin, 1987, pp. 54 to 124.

*Primary Examiner*—Paul Lieberman
*Assistant Examiner*—Necholus Ogde
*Attorney, Agent, or Firm*—Wayne C. Jaeschke; John E. Drach; Henry E. Millson, Jr.

[57] ABSTRACT

New toilet soaps contain: (a1) 4 to 7% by weight alkyl and/or alkenyl oligoglycosides and/or (a2) 2 to 7% by weight fatty acid N-allcylpolyhydroxyalkylamide; (b) 45 to 95% by weight soap and (c) 0 to 10% by weight anionic surfactants selected from the group of alkyl sulphates, isethionates, taurides, sarcosinates, mono- and dialkylsulfosuccinates, ether carboxylic acids, sulphotriglycerides and alkyloligoglucoside sulphates. These new soaps are characterized among others by an improved creaminess, a high foaming power, remarkable cosmetic compatibility with the skin and mechanical firmness.

21 Claims, No Drawings

BAR SOAPS

BACKGROUND OF THE INVENTION

1. Field of the Invention

This invention relates to bar soaps containing alkyl and/or alkenyl oligoglycosides and/or fatty acid N-alkyl polyhydroxyalkylamides, soaps and optionally selected anionic surfactants.

2. Statement of Related Art

Modern bar soaps, more particularly toilet soaps, are normally based on mixtures of beef tallow and coconut oil in a ratio of approximately 9:1. This fatty mixture is hydrolyzed by addition of sodium hydroxide to the base soap to which other additives, including for example humectants, fillers and binders, superfatting agents, dyes and perfumes, etc., are added. Toilet soaps normally contain approximately 80% of fatty acid salts, 10% of water and ad 100% auxiliaries and additives. The large number of products offered to the consumer reflect the vigorous market interest and, at the same time, make it clear that there is a constant demand among consumers for further improved products distinguished in particular by improved dermatological compatibility, greater foaming power, greater creaminess, refatting, removability by rinsing, feeling on the skin and the like. By contrast, soap manufacturers are looking for soap formulations which, for example, lead to bars of greater breaking strength or which enable certain surfactants, for example alkyl sulfates, to be readily incorporated. An overview on this subject can be found, for example, in J. Am. Oil. Chem. Soc. 59, 442 (1982).

So far as the production of bar soaps is concerned, it is readily possible to look back over a very large number of known processes. A clear distinction has to be made in this regard between synthetic "soap-free" soaps, so-called syndets, and in particular combinations of fatty acid salts and synthetic surfactants ("combination bars"). According to EP-A-0 176 330 (Unilever), for example, combination bars are produced by combining fatty acid soaps with salts of isethionic acid. The use of fatty acid isethionates as a synthetic ingredient of combination bars is known from EP-A 0 189 332, EP-A 0 472 320 and EP-A 0 508 006 (Unilever).

Recently, increasing interest has also been shown in alkyl glucosides as a class of nonionic mild surfactants for the production of toilet soaps. For example, it is proposed in a technical bulletin published by Rohm & Haas on "Triton CG-110" to add this $C_{8-10}$ alkyl oligoglucoside to a base soap in quantities of 2% by weight. It is known from DE-AS 593 422 (Th. Boehme) that the addition of 10 to 15% by weight of acetyl maltoside to a base soap mixture produces an improvement in washing power.

U.S. Pat. Nos. 4,536,318 and 4,599,188 (Procter & Gamble) describe foaming mixtures of alkyl glucosides and soaps which are described as being basically suitable for the production of bar soaps. In addition, toilet soaps containing cationic polymers in addition to soaps and alkyl glucosides are known from European patent applications EP-A 0 227 321, EP-A 0 308 189 and EP-A 308 190 (Procter & Gamble).

According to the teaching of U.S. Pat. No. 5,043,091 (Colgate), the addition of alkyl glucosides to soaps containing alkyl benzenesulfonates and alkyl sulfates can improve their mechanical properties at the production stage. Finally, European patent application EP-A 0 463 912 (Colgate) describes toilet soaps containing 45 to 95% by weight of $C_{8-24}$ fatty acid soaps, 1 to 20% by weight of alkyl glucosides, humectants and optionally anionic surfactants and/or fatty acids.

Despite the extensive prior art, the known solutions are still not entirely satisfactory. For example, it is not possible in most cases to dispense with the use of fatty alcohols as plasticizers because otherwise moldability would be unsatisfactory. Some fatty alcohol sulfates and other anionic surfactants are difficult to incorporate in some formulations while formulations containing alkyl glucosides are not sufficiently solid and show a tendency to deliquesce. Several of the products on the market are also not entirely satisfactory in regard to their compatibility, particularly with sensitive skin.

Accordingly, the problem addressed by the present invention was to provide new bar soap formulations having a complex property profile which would be free from the disadvantages mentioned above.

DESCRIPTION OF THE INVENTION

The present invention relates to bar soaps containing a1) 4 to 7% by weight of alkyl and/or alkenyl oligoglycosides and/or a2) 4 to 7% by weight of fatty acid N-alkyl polyhydroxyalkylamides, b) 45 to 95% by weight of soap and c) 0 to 10% by weight of anionic surfactants selected from the group consisting of alkyl sulfates, monoglyceride (ether) sulfates, fatty acid alkanolamide (ether) sulfates, isethionates, taurides, sarcosinates, mono- and dialkyl sulfosuccinates, ether carboxylic acids, sulfotriglycerides and alkyl oligoglucoside sulfates.

It has surprisingly been found that bar soaps which, in addition to fatty acid sodium salts, contain glycosides or glucamides in a concentration of 4 to 7% by weight as synthetic surfactants, show particular advantages in regard to foaming power, foam stability and dermatological compatibility. These properties can be synergistically enhanced by mixing components a1) and a2) with one another and/or by mixing the anionic surfactants selected. The invention includes the observation that bar soaps containing glycosides or glucamides in the quantities mentioned on the one hand show adequate breaking strength, so that there is hardly any need to use plasticizers and, on the other hand, are so solid that they can be permanently mechanically deformed. At the same time, anionic surfactants, particularly alkyl sulfates, may readily be incorporated in the formulations.

Alkyl and/or alkenyl oligoglycosides

Alkyl and alkenyl oligoglycosides are known substances which may be obtained by relevant methods of preparative organic chemistry and which correspond to formula I:

$$R^1O\text{---}[G]_p \qquad (I)$$

in which $R^1$ is a linear or branched alkyl and/or alkenyl radical containing 6 to 22 carbon atoms, G is a sugar unit containing 5 or 6 carbon atoms and p is a number of 1 to 10.

EP-A1-0 301 298 and WO 90/3977 are cited as representative of the extensive literature available on the subject. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization below 1.7 and, more particularly, between 1.2 and 1.4 are preferred from the applicational point of view.

The alkyl or alkenyl radical $R^1$ may be derived from primary alcohols containing 6 to 11 and preferably 8 to 10 carbon atoms. Typical examples are butanol, caproic alcohol, caprylic alcohol, capric alcohol and undecyl alcohol and technical mixtures thereof such as are obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fattyalcohol by distillation and which may contain less than 6% by weight $C_{12}$ alcohol as an impurity, and alkyl oligoglucosides based on technical $C_{9-11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil fatty alcohol having a DP of 1 to 3 are preferred.

In one particular embodiment of the invention, the alkyl and/or alkenyl oligoglycosides may be used in anhydrous form in admixture with polymers obtained, for example, in the spray drying of alkyl oligoglucosides and starch together.

Fatty acid N-alkyl polyhydroxyalkylamides

The fatty acid M-alkyl poiyhydroxyalkylamides correspond to formula (II):

in which $R^2CO$ is an aliphatic acyl radical containing 6 to 22 carbon atoms, $R^3$ is hydrogen, a $C_{1-4}$ alkyl or hydroxyalkyl radical and [Z] is a linear or branched polyhydroxyalkyl radical containing 3 to 12 carbon atoms and 3 to 10 hydroxyl groups.

The fatty acid-N-alkyl polyhydroxyalkylamides are known substances which are normally obtained by reductive amination of a reducing sugar with ammonia, an alkyl amine or an alkanolamine and subsequent acylation with a fatty acid, a fatty acid alkyl ester or a fatty acid chloride. Processes for their production are described in U.S. Pat. No. 1,985,424, U.S. Pat. No. 2,016,962 and U.S. Pat. No. 2,703,798 and in International patent application WO 92/06984. An overview on this subject by H. Kelkenberg can be found in Tens. Surf. Det. 25, 8 (1988).

The fatty acid N-alkyl polyhydroxyalkylamides are preferably derived from reducing sugars containing 5 or 6 carbon atoms, more particularly glucose. Accordingly, the preferred fatty acid N-alkyl polyhydroxyalkylamides are fatty acid N-alkyl glucamides corresponding to formula (III):

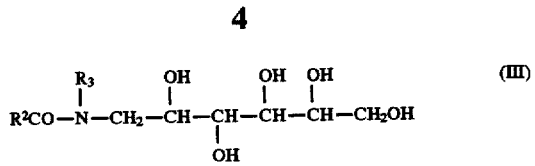

Glucamides corresponding to formula (III), in which $R^3$ is hydrogen or an amine group and $R^2CO$ is the acyl radical of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof, are preferably used as the fatty acid N-alkyl polyhydroxyalkylamides. Fatty acid N-alkyl glucamides (III) obtained by reductive amination of glucose with methyl amine and subsequent acylation with lauric acid or $C_{12/14}$ coconut oil fatty acid or a corresponding derivative are particularly preferred. The polyhydroxyalkylamides may also be derived from maltose and palatinose.

The use of fatty acid N-alkyl polyhydroxyalkyl-amides is also the subject of a number of publications. For example, their use as thickeners is known from European patent application EP-A10 285 768 (Hüls). The use of glucamides in various laundry detergents, dishwashing detergents and cleaning products is described in International patent applications WO 92/6152; 6154; 6155; 6161; 6162; 6164; 6170; 6171 and 6172 (Procter & Gamble). FR-A 1 580 491 (Henkel) describes water-containing detergent mixtures based on sulfates and/or sulfonates, nonionic surfactants and optionally soaps which contain fatty acid N-alkyl glucamides as foam regulators. The use of glucamides in bar soaps is not mentioned in any of these documents.

In one preferred embodiment of the invention, the alkyl and/or alkenyl oligoglucosides and the fatty acid N-alkyl polyhydroxyalkylamides may be used in a ratio by weight of 2:1 to 1:2 and preferably in substantially equal parts by weight. The sum of the two components a1) and a2) may thus again make up 4 to 7% by weight, based on the bar soap.

Soaps

Soaps corresponding to formula (IV):

in which $R^3CO$ is an aliphatic acyl radical containing 6 to 22 carbon atoms and preferably 12 to 18 carbon atoms are suitable for use in accordance with the invention. Typical examples are the sodium salts of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof such as are obtained, for example, in the pressure hydrolysis of natural fats and oils. Technical soap mixtures based on $C_{12-18}$ or $C_{12-14}$ coconut oil fatty acid or $C_{16-18}$ tallow fatty acid are particularly preferred. The quantity of soap used is advantageously between 65 and 85% by weight, based on the bar soap.

Anionic surfactants

The selected anionic surfactants are known substances which may be obtained by the relevant methods of preparative organic chemistry. Particulars can be found, for example, in the synoptic works in J. Falbe (ed.), "Surfactants in Consumer Products", Springer Verlag, Berlin, 1987, pages 54 to 124.

The following surfactants are particularly suitable:

c1) Alkyl sulfates corresponding to formula (V):

$$R^4-O-SO_3Z \quad (V)$$

in which $R^4$ is a linear or branched alkyl radical containing 6 to 22 and preferably 12 to 18 carbon atoms and Z is an alkali metal or alkaline earth metal or ammonium.

c2) Monoglyceride (ether) sulfates obtainable, for example, by transesterification and, optionally, simultaneous ethoxylation of a mixture of coconut oil and glycerol and subsequent sulfonation with sulfur trioxide and neutralization with aqueous bases (cf. WO 92/09569, WO 92/09570, Henkel).

c3) Fatty acid alkanolamide (ether) sulfates corresponding to formula (VI):

$$R^5CO-NH-CH_2CH_2-O-(CH_2CH_2O)_nSO_3Z \quad (VI)$$

in which $R^5CO$ is a linear or branched acyl radical containing 6 to 22 and preferably 12 to 18 carbon atoms, n is 0 or a number of 1 to 10 and Z is an alkali metal or alkaline earth metal or ammonium (cf. WO 93/10084, Henkel).

c4) Isethionates corresponding to formula (VII):

$$R^6CO-OCH_2CH_2-SO_3Z \quad (VII)$$

in which $R^6CO$ is a linear or branched acyl radical containing 6 to 22 and preferably 12 to 18 carbon atoms and Z is an alkali metal or alkaline earth metal or ammonium.

c5) Taurides corresponding to formula (VIII):

$$\underset{R^7CO-N-CH_2CH_2-SO_3Z}{\overset{CH_3}{|}} \quad (VIII)$$

in which $R^7CO$ is a linear or branched acyl radical containing 6 to 22 and preferably 12 to 18 carbon atoms and Z is an alkali metal or alkaline earth metal or ammonium.

c6) Sarcosinates corresponding to formula (IX):

$$\underset{R^8CO-N-CH_2COOZ}{\overset{CH_3}{|}} \quad (IX)$$

in which $R^8CO$ is a linear or branched acyl radical containing 6 to 22 and preferably 12 to 18 carbon atoms and Z is hydrogen, an alkali metal or alkaline earth metal or ammonium.

c7) Mono- and dialkyl sulfosuccinates corresponding to formula (X):

$$\underset{R^9OOC-CH_2CH-COOR^{10}}{\overset{SO_3Z}{|}} \quad (X)$$

in which $R^9$ is a linear or branched $C_{6-22}$ and preferably $C_{12-18}$ alkyl radical optionally substituted by 1 to 10 oligoethylene glycol units, $R^{10}$ is hydrogen, Z or $R^9$ and Z is an alkali metal or alkaline earth metal or ammonium.

c8) Ether Carboxylic acids corresponding to formula (XI):

$$R^{11}O(CH_2CH_2O)_mCH_2COOZ \quad (XI)$$

in which $R^{11}$ is a linear or branched $C_{6-22}$ and preferably $C_{12-18}$ alkyl and/or alkenyl radical, m is a number of 1 to 10 and Z is an alkali metal or alkaline earth metal or ammonium.

c9) Sulfotriglycerides obtainable, for example, by reaction of saturated and/or unsaturated triglycerides with sulfur trioxide and subsequent neutralization with aqueous bases (cf. WO 91/06532, WO 91/19009, Henkel).

c10) Alkyl oligoglucoside sulfates obtainable, for example, by reaction of alkyl oligoglucosides with sulfur trioxide in inert solvents or in the form of a mixture with alkyl sulfates by sulfation of technical mixtures of alkyl oligoglucosides and fatty alcohols (cf. WO 91/13896, Henkel).

Combinations of alkyl oligoglucosides and anionic surfactants are known from the prior art. For example, in Rivista Ital. 10, 567 (1974), G. Proserpio and G Viahello describe shampoos which, in addition to alkyl glucosides, contain sodium lauryl sulfate, coconut oil fatty acid isethionates, coconut oil fatty acid sarcosinates or alkyl sulfosuccinates. The use of short-chain alkyl oligoglucosides together with ether carboxylic acids as constituents of foam baths, shampoos and liquid detergents is known from company literature of C. F. Angele ("NIFANKOL LXK"). EP-A2 0 358 216 (Kao) describes skin-compatible mixtures of alkyl glucosides and sulfosuccinates, more particularly monoalkyl sulfosuccinates, in hair shampoos and dishwashing detergents. Finally, low-foaming detergents containing alkyl oligoglucosides and ether carboxylic acids are proposed in DE-A1 40 16 819 (Hüls).

Combinations of fatty acid N-alkyl glucamides and anionic surfactants are also known from the prior art. For example, mixtures of glucamides with surfactants of sulfate and/or sulfonate structure, ether carboxylic acids, ether sulfates, methyl ester sulfonates and nonionic surfactants are the subject of International patent applications WO 92/6153; 6156; 6157; 6158; 6159 and 6160 (Procter & Gamble).

However, the use of the anionic surfactants mentioned above together with alkyl and/or alkenyl oligoglycosides and/or fatty acid N-alkyl polyhydroxyalkylamides and also fatty acid salts is not discussed in these documents. The selected anionic surfactants may be used in quantities of 1 to 10% by weight and preferably in quantities of 4 to 7% by weight, based on the bar soaps.

Auxiliaries and additives

The bar soaps according to the invention may contain saturated linear fatty acids which correspond to the fatty acid salts used and, accordingly, also preferably contain 12 to 18 carbon atoms as important auxiliaries and additives.

Suitable builders are fine-particle, water-insoluble alkali metal alumosilicates, the use of synthetic crystalline sodium alumosilicates containing bound water being preferred and the use of zeolite A being particularly preferred. Zeolite NaX and mixtures thereof with zeolite NaA may also be used. Suitable zeolites have a calcium binding power of 100 to 200 mg CaO/g. A zeolite NaA containing approx. 20% by weight bound of water commercially obtainable as WESSALITH® P (Degussa) is preferably used in a quantity of 8 to 15% by weight.

As mentioned at the beginning, a particular advantage of the bar soaps according to the invention is that there is little or no need, to use plasticizers or binders. Nevertheless, substances such as these may be present in the formulations for other reasons. Examples of this group of substances are $C_{12-22}$ fatty alcohols, fatty acid glycerides of $C_{12-22}$ fatty acids or corresponding wax esters.

The formulation may also contain nonionic surfactants, for example polyglycol ethers having HLB values of 12 to 18 and/or protein fatty acid condensates, as further constituents. Protein fatty acid condensates have long been commercially obtainable, for example, under the names of LAMEPON® and MAYPON®. It has also proved to be of particular advantage to add w/o emulsifiers from the group of pentaerythritol difatty acid esters and citric acid difatty acid esters.

The auxiliaries and additives may be used in total quantities of 1 to 30% by weight and preferably in total quantities of 2 to 15% by weight, based on the bar soaps.

Production of the bar soaps

The bar soaps according to the invention may be produced by the methods normally used for such products. More particularly, the combination according to the invention of soap with selected quantities of glucosides and/or glucamides gives a particularly easy-to-mold material which is plastic when hot and hard when cold, the molded products having a smooth surface. Conventional processes for mixing or homogenizing, kneading, optionally pilling, extruding, optionally pelleting, extruding, cutting and bar pressing are known to the expert and may be used for the production of the bar soaps according to the invention. The bar soaps are preferably produced at temperatures in the range from 60° to 90° C, the meltable starting materials being introduced into a heatable kneader or mixer and the non-melting components then being stirred in. The mixture obtained may then be passed through a sieve for homogenization before it is subsequently molded.

Industrial Applications

The bar soaps according to the invention are distinguished by particularly high foaming power, good foam stability, creaminess and excellent skin-cosmetic compatibility. They may be formulated with virtually no need for plasticizers or binders and also enable anionic surfactants, particularly alkyl sulfates, to be readily used.

EXAMPLES

I. Substances used

A) Glucosides and glucamides

A1) $C_{12/16}$ Coconut oil alkyl oligoglucoside Plantaren® APG 600 CS-UP, DP degree=1.4

A2) $C_{8/10}$ Alkyl oligoglucoside Plantaren®APG 225 CS-UP, DP degree =1.6

A3) $C_{12/14}$ Coconut oil fatty acid N-methyl glucamide

B) Soaps

B1) $C_{16/18}$ Tallow fatty acid sodium salt

B2) $C_{12/18}$ Coconut oil fatty acid sodium salt

C) Anionic surfactants

C1) Lauryl sulfate Na salt/tallow sulfate Na salt (2:1)

C2) $C_{12/18}$ Coconut oil monoglyceride sulfate Na salt

C3) $C_{12/14}$ Coconut oil fatty acid isethionate $NH_4$ salt

C4) Dilauryl-5EO-sulfosuccinate Na Salt

C5) Monolauryl sulfosuccinate di-Na salt

C6) $C_{12/14}$ Coconut oil fatty alcohol-5EO-ether carboxylic acid Na salt

C7) Sulfo-coconut oil Na salt

C8) $C_{12/14}$ Coconut oil alkyl oligoglucoside sulfate Na salt

Auxiliaries and additives

D1) $C_{16/18}$ Tallow fatty acid

D2) Zeolite NaA (Wessalith® P, a product of Degussa, Hanau/FRG)

D3) Cetostearyl alcohol (1:1)

D4) Cetyl oleyl alcohol·10 EO

D5) Protein hydrolyzate/fatty acid condensate K salt (Lamepon® S, a product of Grünau, Illertissen/FRG)

D6) Water

Unless otherwise stated, the starting materials are commercial products or research products of Henkel KGaA, Düsseldorf, FRG.

II. Formulation Examples

TABLE 1

Formulation examples according to the invention
Percentages in % by weight

|     | F1 % | F2 % | F3 % | F4 % | F5 % | F6 % | F7 % | F8 % |
|-----|------|------|------|------|------|------|------|------|
| A1  | 5    | —    | —    | 2    | 5    | 5    | 5    | 5    |
| A2  | —    | 5    | —    | —    | —    | —    | —    | —    |
| A3  | —    | —    | 5    | 2    | —    | —    | —    | —    |
| B1  | 70   | —    | 70   | 71   | 65   | 65   | 65   | 65   |
| B2  | —    | 70   | —    | —    | —    | —    | —    | —    |
| C1  | —    | —    | —    | —    | 5    | —    | —    | —    |
| C2  | —    | —    | —    | —    | —    | 5    | —    | —    |
| C3  | —    | —    | —    | —    | —    | —    | 5    | —    |
| C4  | —    | —    | —    | —    | —    | —    | —    | 5    |
| C5  | —    | —    | —    | —    | —    | —    | —    | —    |
| C6  | —    | —    | —    | —    | —    | —    | —    | —    |
| C7  | —    | —    | —    | —    | —    | —    | —    | —    |
| C8  | —    | —    | —    | —    | —    | —    | —    | —    |
| D1  | —    | —    | —    | —    | 5    | 5    | 5    | 5    |
| D3  | 12   | 12   | 12   | 12   | 10   | 10   | 10   | 10   |
| D4  | —    | —    | —    | —    | 1    | 1    | 1    | 1    |
| D5  | 5    | 5    | 5    | 5    | 4    | 4    | 4    | 4    |
| D6  | 5    | 5    | 5    | 5    | 2    | 2    | 2    | 2    |
| D7  | 3    | 3    | 3    | 2    | 3    | 3    | 3    | 3    |

|     | F9 % | F10 % | F11 % | F12 % | F13 % | F14 % | F15 % | F16 % |
|-----|------|-------|-------|-------|-------|-------|-------|-------|
| A1  | 5    | 5     | 5     | 5     | 3     | 3     | 3     | 3     |
| A2  | —    | —     | —     | —     | —     | —     | —     | —     |
| A3  | —    | —     | —     | —     | 3     | 3     | 3     | 3     |
| B1  | 65   | 65    | 65    | 65    | 64    | 64    | 64    | 64    |
| B2  | —    | —     | —     | —     | —     | —     | —     | —     |
| C1  | —    | —     | —     | —     | 5     | —     | —     | —     |
| C2  | —    | —     | —     | —     | —     | —     | —     | —     |
| C3  | —    | —     | —     | —     | —     | 5     | —     | —     |
| C4  | —    | —     | —     | —     | —     | —     | 5     | —     |
| C5  | 5    | —     | —     | —     | —     | —     | —     | 5     |
| C6  | —    | 5     | —     | —     | —     | —     | —     | —     |
| C7  | —    | —     | 5     | —     | —     | —     | —     | —     |
| C8  | —    | —     | —     | 5     | —     | —     | —     | —     |
| D1  | 5    | 5     | 5     | 5     | 5     | 5     | 5     | 5     |
| D2  | 10   | 10    | 10    | 10    | 10    | 10    | 10    | 10    |
| D3  | 1    | 1     | 1     | 1     | 1     | 1     | 1     | 1     |
| D4  | 4    | 4     | 4     | 4     | 4     | 4     | 4     | 4     |
| D5  | 2    | 2     | 2     | 2     | 2     | 2     | 2     | 2     |
| D6  | 3    | 3     | 3     | 2     | 3     | 3     | 3     | 3     |

TABLE 2

Comparison formulations
Percentages in % by weight

|     | F17 % | F18 % | F19 % | F20 % | F21 % | F22 % | F23 % | F24 % |
|-----|-------|-------|-------|-------|-------|-------|-------|-------|
| A1  | 3     | —     | 1     | 10    | —     | 10    | 10    | 10    |
| A2  | —     | —     | —     | —     | —     | —     | —     | —     |
| A3  | —     | 3     | 1     | —     | 10    | —     | —     | —     |
| B1  | 72    | —     | 73    | 65    | 65    | 60    | 60    | 60    |
| B2  | —     | 72    | —     | —     | —     | —     | —     | —     |
| C1  | —     | —     | —     | —     | 5     | —     | —     | —     |
| C2  | —     | —     | —     | —     | —     | —     | —     | —     |

TABLE 2-continued

| | Comparison formulations Percentages in % by weight | | | | | | | |
|---|---|---|---|---|---|---|---|---|
| | F17 % | F18 % | F19 % | F20 % | F21 % | F22 % | F23 % | F24 % |
| C3 | — | — | — | — | — | — | 5 | — |
| C4 | — | — | — | — | — | — | — | — |
| C5 | — | — | — | — | — | — | — | 5 |
| C6 | — | — | — | — | — | — | — | — |
| C7 | — | — | — | — | — | — | — | — |
| C8 | — | — | — | — | — | — | — | — |
| D1 | — | — | — | — | 5 | 5 | 5 | 5 |
| D3 | 12 | 12 | 12 | 12 | 10 | 10 | 10 | 10 |
| D4 | — | — | — | — | 1 | 1 | 1 | 1 |
| D5 | 5 | 5 | 5 | 5 | 4 | 4 | 4 | 4 |
| D6 | 5 | 5 | 5 | 5 | 2 | 2 | 2 | 2 |
| D7 | 3 | 3 | 3 | 2 | 3 | 3 | 3 | 3 |

III. Foaming power

Foaming power (base foam and foam collapse after 3 to 5 minutes) was determined by the Ross-Miles test (DIN 53 902-II) using 1 g active substance in water at 20° C./16° d. Evaluation is sensibly based not on the bar soaps, but instead on the surfactant components present therein. Accordingly, mixtures of components a), b) and optionally c) corresponding to formulations F1 to F16 according to the invention and comparison formulations F17 to F24 were prepared and tested. To this end, the surfactant contents (a+b+c) were converted to 100% by weight. Direct comparison is possible because all the Formulation Examples have a surfactant content of 75% by weight. The results are set out in Table 3:

TABLE 3

| | | Foaming power | | |
|---|---|---|---|---|
| | | Foam height in ml after | | |
| Ex. | Formulation | 0 min. | 3 mins. | 5 mins. |
| 1 | F1 | 205 | 190 | 175 |
| 2 | F2 | 200 | 180 | 170 |
| 3 | F3 | 210 | 200 | 185 |
| 4 | F4 | 220 | 210 | 195 |
| 5 | F5 | 220 | 200 | 185 |
| 6 | F6 | 215 | 200 | 185 |
| 7 | F7 | 220 | 205 | 190 |
| 8 | F8 | 220 | 200 | 185 |
| 9 | F9 | 220 | 205 | 180 |
| 10 | F10 | 220 | 200 | 185 |
| 11 | F11 | 220 | 205 | 185 |
| 12 | F12 | 220 | 200 | 180 |
| 13 | F13 | 250 | 230 | 210 |
| 14 | F14 | 240 | 220 | 210 |
| 15 | F15 | 240 | 220 | 215 |
| 16 | F16 | 240 | 220 | 215 |
| C1 | F17 | 150 | 130 | 100 |
| C2 | F18 | 120 | 100 | 80 |
| C3 | F19 | 170 | 150 | 135 |
| C4 | F20 | 210 | 200 | 190 |
| C5 | F21 | 210 | 200 | 190 |
| C6 | F22 | 190 | 180 | 160 |
| C7 | F23 | 200 | 180 | 165 |
| C8 | F24 | 200 | 180 | 165 |

The Examples show the following:

The tallest and most stable foam is obtained with mixtures of alkyl oligoglucosides, fatty acid alkyl glucgmides, soaps and the selected anionic surfactants within the mixing ratios mentioned (formulations F13 to F16; Examples 13 to 16);

A tall and stable foam is also obtained with mixtures of alkyl oligoglucosides or fatty acid amides with soap and optionally anionic surfactants (formulations F1 to F12; Examples 1 to 12);

If the percentage content of alkyl oligoglucosides and/or fatty acid alkyl glucamides in the formulations is reduced below a critical value of 4% by weight, based on the bar soap, the height of the base foam decreases significantly (formulations F17–F18; Comparison Examples C1–C3);

If the percentage content of alkyl oligoglucosides and/or fatty acid alkyl glucamides in the formulations is increased beyond a critical value of 7% by weight, based on the bar soap, a sufficiently tall and stable foam is obtained (formulations F20, F21; Comparison Examples C4, C5), but unfortunately the formulations are too soft, gradually deliquesce and are therefore unsuitable for the production of bar soaps. Moreover, the foam level of formulations F13 to F16 is not reached.

Although the volume of foam is reduced again by addition of anionic surfactants to comparison formulation F20, the formulations undergo a slight increase in strength (formulations F22 to F24; Comparison Examples C6 to C8). In the case of formulation F22, the anionic surfactant component—lauryl sulfate—could not be homogeneously incorporated.

What is claimed is:

1. A bar soap comprising: (a) an alkyl oligoglucoside an alkenyl oligoglycoside, or a combination thereof; (b) a fatty acid-N-alkyl polyhydroxyalkylamide; (c) from about 45 to about 95% by weight of soap; (d) from 0 to about 10% by weight of anionic surfactant selected from the group consisting of alkyl sulfates, monoglyceride (ether) sulfates, fatty acid alkanolamide (ether) sulfates, isethionates, taurides, sarcosinates, mono- and dialkyl sulfosuccinates, ether carboxylic acids, sulfotriglycerides and alkyl oligoglucoside sulfates; wherein the ratio by weight of component (a) to component (b) is from 2:1 to about 1:2 and the total weight of component(a) plus component (b) is from 4 to 7%.

2. The bar soap of claim 1 wherein said alkyl or alkenyl oligoglycoside is a compound of the formula (I);

wherein $R^1$ is a linear or branched alkyl and/or alkenyl radical having from 6 to 22 carbon atoms, G is a sugar unit having 5 or 6 carbon atoms and p is a number of 1 to 10.

3. The bar soap of claim 1 wherein said fatty acid N-alkyl polyhydroxyalkylamide is a compound of the formula (II):

wherein $R^2CO$ is an aliphatic acyl radical having from 6 to 22 carbon atoms, $R^3$ is hydrogen, a $C_{1-4}$ alkyl or hydroxyalkyl radical and (Z) is a linear or branched polyhydroxyalkyl radical having from 3 to 12 carbon atoms and 3 to 10 hydroxyl groups.

4. The bar soap of claim 1 wherein said soap is a compound of the formula (IV)

wherein $R^3CO$ is an aliphatic acyl radical having from 6 to 22 carbon atoms.

5. The bar soap of claim 1 wherein the amount of said anionic surfactant is from 1% to 10% by weight.

6. The soap bar of claim 1 further comprising a saturated linear fatty acid, a builder, or a combination thereof.

7. The bar soap of claim 2 wherein the oligoglycoside is an oligoglucoside.

8. The bar soap of claim 2 wherein p is a number of from 1 to about 6.

9. The bar soap of claim 8 wherein p is a number of from about 1.1 to about 3.0.

10. The bar soap of claim 7 wherein p is a number of from about 1.2 to about 1.4.

11. The bar soap of claim 2 wherein the $R^1$ radical contains from 6 to 11 carbon atoms.

12. The bar soap of claim 2 wherein the $R^1$ radical contains from 12 to 14 carbon atoms.

13. The bar soap of claim 4 wherein $R^3CO$ contains from 12 to 18 carbon atoms.

14. The bar soap of claim 7 wherein from about 65 to about 85% by weight of component (c) is present therein.

15. The bar soap of claim 1 wherein from about 4 to about 7% by weight of component (d) is present therein.

16. The bar soap of claim 1 wherein component (b) is a glucamide.

17. The bar soap of claim 1 wherein component (a) is a compound of the formula (I):

$$R^1O\text{—}(G)_p \qquad (I)$$

wherein $R^1$ is a linear or branched alkyl and/or alkenyl radical having from 6 to 22 carbon atoms, G is a sugar unit having 5 or 6 carbon atoms and p is a number of I to 10; component (b) is a compound of the formula (II):

wherein $R^2CO$ is an aliphatic acyl radical having from 8 to 22 carbon atoms, $R^3$ is hydrogen, a $C_{1-4}$ alkyl or hydroxyalkyl radical and (Z) is a linear or branched polyhydroxyalkyl radical having from 3 to 12 carbon atoms and 3 to 10 hydroxyl groups; and component (c) is a compound of the formula (IV)

$$R^3CO\text{—}ONa \qquad (IV)$$

wherein $R^3CO$ is an aliphatic acyl radical having from 6 to 22 carbon atoms.

18. The bar soap of claim 17 wherein the amount of component (d) is from 1% to 10% by weight.

19. The bar soap of claim 17 wherein component (a) is an oligoglucoside and component (b) is a glucamide.

20. A method for increasing foam in a bar soap containing from about 45 to about 95% by weight of soap comprising adding thereto from about 1 to about 10% by weight of an isethionate, and a foam enhancing quantity of an alkyl oligoglycoside, an alkenyl oligoglycoside, or a combination of said oligoglycosides.

21. The method of claim 20 wherein the isethionate is a coconut oil fatty acid isethionate.

* * * * *